(12) United States Patent
Mir

(10) Patent No.: US 10,316,355 B2
(45) Date of Patent: Jun. 11, 2019

(54) NANOPIPETTE ANALYSIS OF POLYMERS

(71) Applicant: Kalim Mir, Cambridge, MA (US)

(72) Inventor: Kalim Mir, Cambridge, MA (US)

( * ) Notice: Subject to any disclaimer, the term of this patent is extended or adjusted under 35 U.S.C. 154(b) by 0 days.

(21) Appl. No.: 15/328,704

(22) PCT Filed: Jul. 24, 2015

(86) PCT No.: PCT/US2015/042123
§ 371 (c)(1),
(2) Date: Jan. 24, 2017

(87) PCT Pub. No.: WO2016/015018
PCT Pub. Date: Jan. 28, 2016

(65) Prior Publication Data
US 2017/0211135 A1    Jul. 27, 2017

Related U.S. Application Data

(60) Provisional application No. 62/029,382, filed on Jul. 25, 2014.

(51) Int. Cl.
| | |
|---|---|
| C12Q 1/6825 | (2018.01) |
| G01Q 60/44 | (2010.01) |
| G01N 33/543 | (2006.01) |
| B01L 3/02 | (2006.01) |
| G01N 33/487 | (2006.01) |
| C12Q 1/6869 | (2018.01) |
| B82Y 5/00 | (2011.01) |

(52) U.S. Cl.
CPC .......... *C12Q 1/6825* (2013.01); *B01L 3/021* (2013.01); *C12Q 1/6869* (2013.01); *G01N 33/48721* (2013.01); *G01N 33/5438* (2013.01); *G01Q 60/44* (2013.01); *B01L 2200/0663* (2013.01); *B01L 2200/143* (2013.01); *B01L 2300/0896* (2013.01); *B01L 2400/043* (2013.01); *B01L 2400/0415* (2013.01); *B01L 2400/0421* (2013.01); *B01L 2400/0487* (2013.01); *B82Y 5/00* (2013.01)

(58) Field of Classification Search
IPC ..................... B01L 2400/021; C12Q 2565/601
See application file for complete search history.

(56) References Cited

U.S. PATENT DOCUMENTS

| | | | | |
|---|---|---|---|---|
| 2002/0056651 | A1* | 5/2002 | Akeson ............... | C12Q 1/6869 205/775 |
| 2010/0072080 | A1* | 3/2010 | Karhanek .......... | G01N 27/4035 205/792 |
| 2016/0024567 | A1* | 1/2016 | Balagurusamy ............................ | G01N 27/44791 204/451 |

FOREIGN PATENT DOCUMENTS

WO    WO 2014160036    * 10/2014

OTHER PUBLICATIONS

Karhanek et al, Single DNA Molecule Detection Using Nanopipettes and Nanoparticles, 2005, 5, 403-407. (Year: 2005).*

* cited by examiner

*Primary Examiner* — Narayan K Bhat
(74) *Attorney, Agent, or Firm* — Morgan, Lewis & Bockius LLP

(57) ABSTRACT

The disclosure relates to devices and instruments for detecting and individually analyzing biomolecules, biomolecular complexes and biomolecules with ligands attached thereon.

22 Claims, 2 Drawing Sheets
Specification includes a Sequence Listing.

NANOPIPETTE ANALYSIS OF POLYMERS

RELATED APPLICATION

This application claims priority under 35 U.S.C. § 119 to U.S. provisional patent application, U.S. Ser. No. 62/029,382, filed Jul. 25, 2014, entitled "NANOPIPETTE ANALYSIS OF POLYMERS," the entire contents of which are incorporated herein by reference.

Sequence Listing Submission Via EFS-Web

A computer readable text file, entitled "SequenceListing.txt," created on or about Jul. 24, 2015 with a file size of about 1 kb contains the sequence listing for this application and is hereby incorporated by reference in its entirety.

BACKGROUND

It is increasingly realized that single molecule analysis techniques provide a depth of analysis not possible with traditional ensemble molecular methods. Gel analysis, microarray analysis and other methods that are commonly used in biochemistry and molecular biology take averaged readings of thousands of molecules. The target molecules typically have to be purified in substantial quantities (e.g., proteins) or must be amplified by PCR (e.g., DNA).

Massively parallel clonal DNA sequencing (e.g., Illumina sequencing) has revolutionized the way we conduct much of the tasks in molecular biology. However there remain a number of drawbacks. The sample material has to be processed and amplified before it can be sequenced. Due to PCR bias, coverage across the genome is not even, which makes de novo assembly challenging for large complex genomes. Typically, the molecules that are analyzed are not long enough length to detect structural variation (SV) and haplotypes are not resolved. Moreover, it is not currently possible to sequence molecules from a single cell without amplification. In the case of proteins, it is challenging to decipher the identity of molecules within a complex mixture unless they are at high abundance. There are a number of methods for analyzing single molecules, including those that require labeling and those that do not. Fluorescence labeling and optical detection has been used as a means for sequencing DNA at the single molecule level (Helicos; Pacbio). An advantage of optical methods is that a large number of single molecules arrayed on a surface can be analyzed in parallel. Due to the diffraction limit of light, the single molecules need to be arrayed at a density that enables individual molecules to be resolved; for example for a fluorophore emitting at 600 nm, the distance is typically 300 nm. In the currently dominant sequencing technology (Bentley, Illumina), such well-spaced single molecules can be amplified in situ to produce clonal clusters which are then sequenced by monitoring the template-directed incorporation of fluorescent nucleotides (sequencing-by-synthesis; SbS). One disadvantage of this approach is that it is not possible to keep all the molecules in synchrony (or in phase) and as the number of cycles increases the errors accumulate. However, the arrayed single molecules need not be amplified and sequencing can be conducted directly on the single molecules, as is done using the Helicos technology [Harris et al], Oxford nanopores technology, PacBio technology [Eid et al]. While such sequencing of single molecules directly does not suffer from the phasing problem, it can be compromised by the photophysics of individual fluorophores.

While it is possible to sequence single molecules of nucleic acids, there are apparently no single molecule methods for sequencing proteins. Moreover, there are no amplification methods for proteins and proteins must be relatively pure and not part of a highly complex mixture in order to be analyzed.

From the foregoing it is clear that although progress has been made, there are a number of deficiencies in the technologies that represent the state of the art.

SUMMARY OF DISCLOSURE

Aspects of the disclosure relate to methods for analysis of polymers and other similar molecules. In some embodiments, an array of polymers are attached to a surface in a manner that renders a substantial part of each polymer free for analysis. In some embodiments, a nanopipette (with or without an integrated nanopore) is brought into proximity of an individual polymer in the array. In some embodiments, the nanopipette contains a fluid and the polymer is bathed in a fluid. In some embodiments, a potential difference (electrical or pressure) is applied between the fluid in the nanopipette and the fluid outside the nanopipette. In some embodiments, the potential difference in the fluid facilitates said polymer entering into the nanopipette and allows it to become elongated while remaining anchored to the surface. In some embodiments, the nanopipette is translated along the longitudinal length of the polymer. In some embodiments, measurements are made during the time period of translation of the nanopipette. In some embodiments, measurements are qualitatively and/or quantitatively a function of the identity of sub-units along the polymer. In the case of DNA or RNA, in some embodiments, there are 4 or 5 basic subunits (e.g., A, G, T, U, C) plus modified versions thereof, e.g., methyl C, hydroxymethyl C. In peptides or polypeptides, in some embodiments, there are 23 basic subunits (e.g., Alanine (A, Ala), Cysteine (C, Cys), Aspartic acid (D, Asp), Glutamic acid (E, Glu), Phenylalanine (F, Phe), Glycine (G, Gly), Histidine (H, His), Isoleucine (I, Ile), Lysine (K, Lys), Leucine (L, Leu), Methionine (M, Met), Asparagine (N, Asn), Pyrrolysine (O, Pyl), Proline (P, Pro), Glutamine (Q, Gln), Arginine (R, Arg), Serine (S, Ser), Threonine (T, Thr), Selenocysteine (U, Sec), Valine (V, Val), Tryptophan (W, Trp), and Tyrosine (Y, Tyr)) and variants thereof (e.g., glycosylated versions).

In some embodiments, the measurements can be repeated by reversing and repeating the translocation. In some embodiments, obtained measurement versus time traces are separated into units of measurement or motifs and the motifs are compared to a database of previously measured or calculated motifs which enables the identification of the contiguous arrangement of units along the polymer. In some embodiments, once one polymer has been analyzed a next polymer can be analysed by translating the nanopipette to the location of the next polymer.

According to some aspects, the present disclosure solves a number of problems found in existing approaches. In some embodiments, the disclosure overcomes issues associated with a low rate of polymer reaching a pore or nanopipette. In some embodiments, methods are provided that involve locating pores to a position that is in sufficient proximity to sample molecules (e.g., polymers) rather than bringing the molecules in proximity to the pores. In some embodiments, methods provided herein are more flexible than conventional approaches, allowing analysis to be done in situ, for example.

In some embodiments, providing sample molecules in an array format makes them readily accessible to a nanopipette, minimizing lag time between measurements. In some embodiments, methods provided in the disclosure controls the rate of translocation of a polymer through a pore such that it is not too rapid for detection, by immobilizing one end of the polymer, then elongating the polymer and then translating the nanopipette along the longitudinal length of the polymer at a controllable speed. The stretching of the polymer from the surface, enables the random motion of the polymer to be substantially reduced enabling clearer identification of signals in the recordings to be made.

In some embodiments, methods of analyzing a polymer are provided which comprise immobilizing polymer strands onto a surface, each being immobilized via one of their termini. In some embodiments, said surface and polymer strands are contained within an electrolyte solution. However, in some embodiments, if the nanopipette is double-barreled the polymer need not already be contained in an electrolyte solution. In some embodiments, said electrolyte solution is in contact with a first electrode. In some embodiments, the methods further comprises approaching one individual polymer strand on the surface with a nanopipette containing an electrolyte solution, said electrolyte solution in contact with a second electrode. In some embodiments, the methods further comprise providing a positive or negative bias to the first electrode to allow an ionic current to flow between the first electrode and the second electrode to facilitate entry of the polymer strand into the internal bore of the nanopipette. In some embodiments, the methods further comprise determining a signal as the polymer passes a specific location in the internal bore of the nanopipette. In some embodiments, the methods further comprise translating the nanopipette with respect to the surface so that more or less of polymer occupies the nanopipette. In some embodiments, the methods further comprise correlating electrical signals with coordinates of the nanopipette.

Aspects of the disclosure relate to methods for analyzing a chain-like macromolecule. In some embodiments, the methods comprise passing one said macromolecule through a nanopipette containing a lipid bilayer and a biological nanopore. In some embodiments, the methods further comprise serially measuring (e.g., directly or indirectly) a physical property of residues within the chain-like macromolecule as each consecutive residue in the macromolecule passes the nanopores. In some embodiments, the methods are particularly useful when applied to DNA, RNA, chromatin, polypeptides or other similar polymeric molecules or molecular complexes.

In some aspects of the disclosure, a method for analyzing or sequencing a polynucleotide (e.g., DNA, RNA) is provided that comprises providing a nanopipette containing a lipid bilayer and a biological nanopore. In some embodiments, the method further comprises providing a positive electrical bias between the inside and outside of the nanopipette. In some embodiments, the method further comprises passing a polynucleotide strand through the nanopipette containing the lipid bilayer and a biological nanopore. In some embodiments, the method further comprises serially measuring (directly or indirectly) a physical property of bases as the polynucleotide translocates through the nanopores. In some embodiments, the method further comprises chopping the traces of the measurements against time, into units representing single bases or a few bases. In some embodiments, the method further comprises matching the units against a database of measurements of known bases and making a base call. In some embodiments of the method, the polynucleotide is disposed on a surface. In some embodiments of the method a nano-motor (e.g., molecular motor such as a helicase or a polymerase) is used to control the translocation of the polynucleotide through the pore.

Further aspects of the disclosure relate to methods for analyzing or sequencing a polypeptide that comprise providing a nanopipette containing a lipid bilayer and a biological nanopore. In some embodiments, the methods further comprise providing a positive or negative electrical bias between the inside and outside of the nanopipette. In some embodiments, the methods further comprise passing a polypeptide strand through the nanopipette containing the lipid bilayer and a biological nanopore. In some embodiments, the methods further comprise serially measuring (directly or indirectly) a physical property of bases as the polypeptide translocates through the nanopores. In some embodiments, the methods further comprise chopping the traces of the measurements against time, into units representing single amino acid or a few amino acids. In some embodiments, the methods further comprise matching the units against a database of measurements of known amino acids and making an amino acid call. In some embodiments of the methods, the polypeptide is disposed on a surface. In some embodiments, a nano- or molecular motor is used to control the translocation of the polypeptide through the pore. Another aspect of the disclosure relates to a method for analyzing a polynucleotide with attached ligands (e.g., chromatin comprising histones attached to DNA).

In some embodiments, the methods comprise providing a nanopipette. In some embodiments, the methods further comprise providing a positive electrical bias between the inside and outside of the nanopipette. In some embodiments, the methods further comprise passing the polynucleotide with attached ligands through the nanopipette. In some embodiments, the methods further comprise serially measuring (directly or indirectly) a physical property of the attached ligands as the polynucleotide translocates through the nanopores. In some embodiments, the methods further comprise extracting the units characteristic of ligands (e.g., increased current blockage) from the measurements versus time traces. In some embodiments, the methods further comprise matching the units against a database of measurements of known ligands attached to polynucleotides and identifying each ligand in the measurements. In some embodiments, the ligands may be attached to labels that facilitate differentiation of different ligands. In some aspects, the disclosure relates to a method of analyzing a complete inventory of molecule(s). In some embodiments, the methods involve accessing a container comprising a complete inventory of molecules using a nanopipette and analyzing each molecule of said inventory one-by-one by making measurements as each molecule traverses past a detection point. In some embodiments multiple populations of polymers are analysed simultaneously, each polymer within each population is tagged with a distinct population-specific label (e.g., sequence). The label is then read alongside the analysis of the polymer. Based on the tag, the data obtained can then optionally be partitioned according to from which population the polymer originated.

In some embodiments the disclosure comprises an instrument comprising an electrical and mechanical components and in some embodiments optical components are included in the instrument. The instrument serves to couple the nanopipette to the samples on a substrate, to control the distance of the nanopipetted from the surface via ionic current measurement, to translate the nanopipette 2-dimensionally over the surface and to interrogate the sample via ionic current or other electrical or optical measurement.

In some embodiments the disclosure comprises a device which is mountable on the instrument which comprises substrate onto which the sample is attached and contains a barrier to confine and retain buffer and electrolyte solutions and an opening for access of the nanopipette to the sample.

In some embodiments the disclosure comprises a kit that is used with the instrument. The kit includes a substrate in which to array the sample molecules, a nanopipette (optionally lipids and a biological pore such as MspA), buffered solutions and electrolyte solution.

DETAILED DESCRIPTION OF DISCLOSURE

Figure 1:
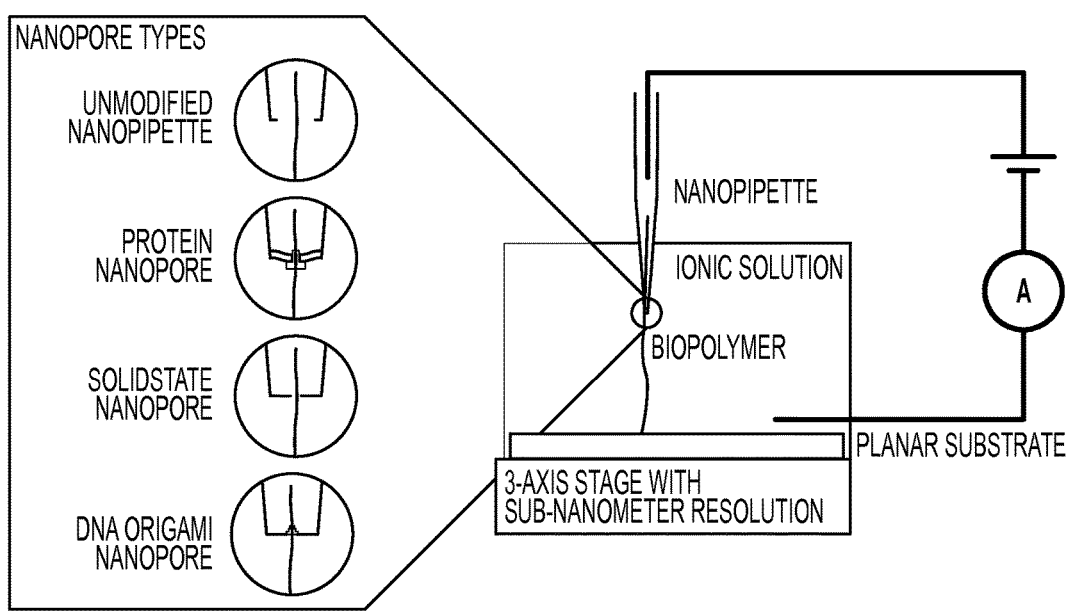
FIG. 1 provides a non-limiting illustration of a nanopipette system.

In some aspects, the disclosure concerns methods, devices, apparatus/instruments, and kits for analyzing macromolecules, supramacromolecules and macromolecular complexes, individually. In another aspect the disclosure provides algorithms. One algorithm is for control and operation of the analysis. Another algorithm is for converting the electrical recordings into biologically meaningful data, e.g., a DNA base determination or call.

Short or medium length molecules can be arrayed on a surface.

Very long molecules (100 s to Mega-base pairs) can be arrayed and stretched out on a surface. Molecular combing methods may be used to stretch individual molecules by anchoring them from one end and then stretching them via the forces created in a receding meniscus of liquid. Aspects of the disclosure relate to methods for sequencing such long molecules (e.g., in their entireties). In some embodiments, it is advantageous to obtain sequence in a long-range context, as the location and number of copies of segments of genomic sequence affect phenotype. Phenotype is also affected by whether specific alleles co-occur on the same chromosome (are in phase) or are dispersed over homologous chromosomes.

As with DNA, for proteins too, rather than obtaining short range sequence information (via fragmentation into peptides) it is important to obtain sequence information in its full length context. This is because a given protein containing a specific first allele may contain a specific second allele at a distal site or may be linked to a protein modification (neither of which are covered by the short peptide). As disclosed herein, nanopore technology is a single molecule technology that may be effectively applied to analyze both proteins and nucleic acids. The nanopipette is versatile, as well as manipulating the polymer, sucking it inside, and making electrical measurements, it can also be used to deliver reagents to the polymers (or to biomolecules or biomacromolecules). The nanopipette can be filled with the reagent by sucking it up (actively or in some cases just by capillary action) from a well or droplet or by the reagent being fed through the top end of the nanopipette. The reagents can be delivered to the sample molecules in the array before nanopipette analysis is conducted or delivery to each polymer can be done while it is inside the nanopipette, directly followed by analysis. For example, for a DNA polymer, a methyl-binding protein such as MBD1 and MBD2 can be delivered to the individual DNA molecule by flooding the biomolecule with the solution containing MBD2. The solution can be actively ejected for example using a piezo, or it can be deposited by contact printing. In some embodiments, a nanopipette or similar device is useful for: biopolymer sequencing; mapping features or ligand binding on biopolymers; achieving selective delivery of reagents to one or a few polymers at specific locations on a surface; and synthesizing a polymer and checking the fidelity of synthesis.

Accordingly, in some embodiments, methods are provided that involve passing a polymer through a nano-scale hole, typically a biological ion channel such as alpha-hemolysin or MspA, where the pore is just wide enough to allow polynucleotides (single strands) or polypeptides to translocate through. In some embodiments, the linear length of the polymer passes through the pore, such that ion blockade events characteristic of specific residues of the polymer that occupy the pore lumen at any given time can be measured by recording the ionic current. In some embodiments, the limited space around the strand in the pore lumen means that small changes in ionic flux can be detected by using amplifiers such as the Axonpatch B (Molecular Devices). The pattern of electrical recordings over time, can be interpreted to reveal the sequence of the polymer.

In some embodiments, methods provided herein are advantageous because they control the extent to which molecules find a pore, ensuring that it occurs at a fast enough rate from one molecule to the next. Also, in some embodiments, methods provided herein ensure that the translocation of the molecules through a pore is controlled and measurements can be made repetitively thereon. In some embodiments, controlling the rate in this manner is advantageous because it enables sufficient throughput and overcomes issues associated with low concentrations of sample. In addition, in some embodiments, small sample amounts can be immobilised over a small area to which the nanopipette can be positioned and individual molecules can be analysed in rapid succession. In contrast to conventional nanopores approaches where low sample amounts are present in relatively large sample volumes, meaning that it takes a long time between one molecule entering the pore and the next. In some embodiments, methods provided herein attenuate the speed in which the polymer translocates through the pore in order for electrical measurement systems to make the required high definition recordings.

To date, certain approaches have used biological "motor" proteins to ratchet the polymer through pores. In some embodiments, it has been recognized that when the speed is attenuated the throughput of nanopore sequencing compared to highly parallel fluorescence-based sequencing can be low. Therefore a large number of pores need to be operated in parallel; this is challenging but progress is being made in this direction For DNA, despite presence of a high error rate, the approach may be sufficiently developed for certain applications. For proteins, aspects of the disclosure relate to a recognition that amino acid detection can be improved by passing polypeptides while taut, through pores.

Figure 2:
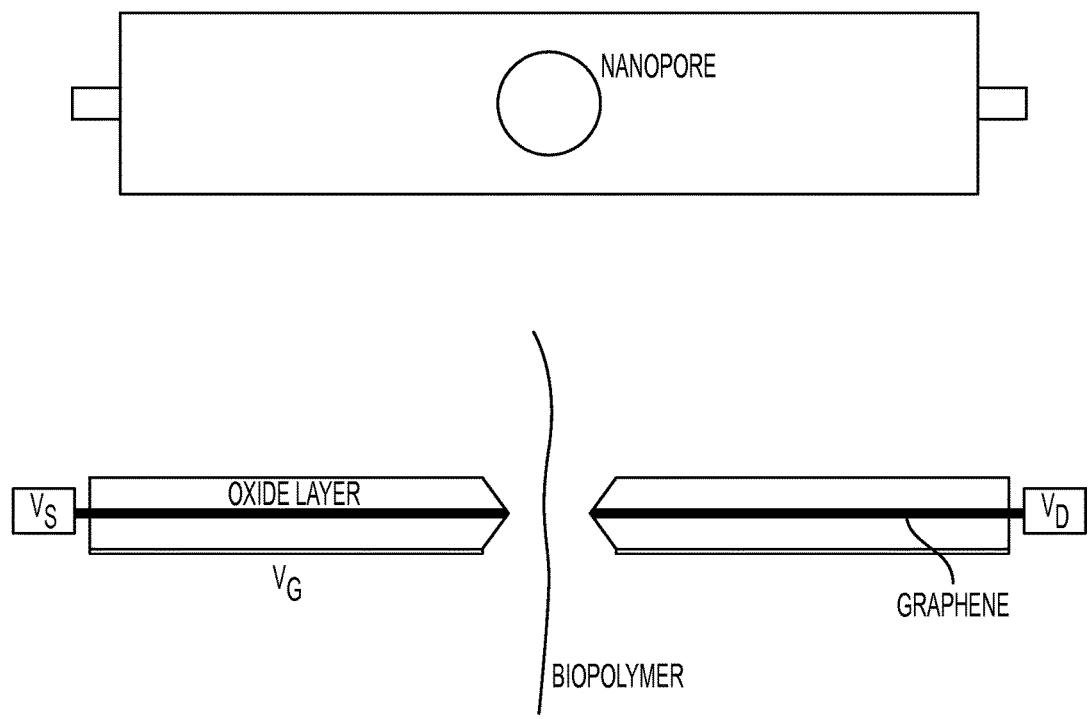
FIG. 2 provides a non-limiting illustration of a graphene-based nanopore.

In addition to biological pores, solid-state nanopores may be used. This includes pores made in substrates such as silicon nitride and graphene involving nanofabrication methods, as shown, for example, in FIG. 2, which provides a schematic example of a grapheme solid-state nanopore configuration that is contained within the tip of the nanopipette.

In some embodiments, the disclosure relates to use of nanopipettes which typically have a 50 nm orifice (Keyser- Steinbock et al Nano Lett., 2010, Edel10 (7), pp 2493-2497, AlbrechtGong et al, d MelloAnal. Chem. 2014, 86, 835-841). Nanopipettes can be readily made using a bench-top pulling device (Sutter Instruments) used routinely in microinjection labs, for example. However, in some embodiments, an orifice width of 50 nm is not narrow enough to be conducive to sequencing. Nanopipettes are useful for a wide range of applications, including microinjection, deposition and scanning probe microscopy (SPM) (Takami et al. Nano Convergence 2014, 1:17). One SPM mode that uses nanopipettes is Scanning Electrochemical Microscopy (SECM) and another is Scanning Ion Conductance Microscopy (SICM), which has been used for analyzing soft biological samples by hovering or hoping above them.

Lipid bilayers and protein nanopores such as alpha hemolysin can be inserted into the nanopipette which results in lower noise, capacitance effects and increased robustness compared to conventional nanopore systems. The Nanopatch (Electrical Biosciences, Utah, USA) can be used to make low noise electrical measurements.

Nanopipette and its Translation in X, Y and Z

Aspects of the disclosure relate to a device, apparatus, or instrument comprising a nanopipette, such as is depicted in FIG. 1.

FIG. 1 depicts a schematic of nanopipette measurement of a single biopolymer attached to a surface. The expanded window shows four possible tip configurations, an anmodified nanopipette, a nanopipette with a lipid bilayer and an protein nanopores, a solid-state nanopores and a DNA origami nanopore.

In some apparatus a nanopipette is connected to devices that enable its movement in the x, y and/or z directions. These devices can comprise piezo-actuators. Instead of, or in addition to, the translation of the nanopipette in the x, y and/or z direction, the surface to which the molecules under analysis are attached can also be translated in the x, y, and z directions.

In some embodiments the apparatus comprises at least one electrode in fluidic contact with the sample. Preferably the interior of the nanopipette contains a first electrode which is in fluidic contact with a second electrode in solution exterior to the nanopipette. Preferably the first electrode is close to the end of the nanopipette opposite the end containing the orifice that first approaches the sample. In some embodiments the exterior and interior solutions comprise electrolytes.

After analyzing a first polymer the nanopipette can dissociate from the polymer and analyse a second polymer, and then a third and so on. An array of nanopipettes can be provided so that a plurality of polymers can be analyzed substantially simultaneously. The array of nanopores also provides multiple chances of capturing a polymer.

The interior of the nanopipette contains a solution and said solution is in fluidic contact with a second electrical contact or electrode. The solution is typically an electrolyte.

Typically the end of the nanopipette facing the surface is tapered, and there is a constriction at or close to the orifice. This is the point where the passage for the ionic current is narrowest. Any changes in ionic current passing this point can be detected in the electrical recordings. Alternatively, a constriction can be placed at any point along the inside of the nanopipette. Multiple constrictions can be placed in the nanopipette but ideally in this case, measurements are made at each constriction.

Electrical recordings are made over time and a time trace can be obtained. The electrical-time trace can be monitored in real-time to detect and determine the character of the features along the polymer length that are at the constriction at any given time. The closer the inner electrode is to the constriction the more closely the real-time activity can be monitored.

An advantage of the nanopipette approach is that the inner or outer parts of the nanopipette(s) can just be dipped into any liquid, containing any substance that one wishes to coat or attach to the nanopipette. To coat the nanopipette with polyacrylamide, the nanopipette is briefly dipped into a solution containing acrylamide, bis-acrylamide and Temed, before it becomes set. To coat the nanopipette with a biological material the nanopipette is dipped into a buffer solution containing that biomaterial e.g., BSA or Casein (milk protein).

In a further aspect the disclosure comprises additional functionality engineered into the nanopipette. Compartments or flow lines for reagent storage and/or delivery or sample collection can be provided in a part of the nanopipette other than the orifice. The back end of the nanopipette can be fabricated to have delivery lines integrated. The delivery lines may deliver processing reagents and wash reagents. Alternatively, the nanopipette can first be positioned in a reservoir containing reagents of interest, a reagent of interest is sucked in, and then the position of the nanopipette is translated to a location which may already contain the polymers of interest.

In some embodiments the nanopipette is a double-barreled nanopipette. The double-barreled nanopipette [R. Adam Seger, P. Actis, C. Penfold, M. Maalouf, B. Vilozny and N. Pourmand, Nanoscale, 2012, 4, 5843-5846; EP 2681304 A2] can create its own current and hence there is no need to have a separate electrode in the sample vessel. One barrel contains the negative electrode and the other one contains the positive electrode. When the analyte is DNA, the negatively charged DNA moves into the barrel containing the positive electrode. The barrel containing the negative electrode can also be loaded with reagents that can be pass into the barrel containing the positive electrode so that they may interact with the DNA. The reagents can include various types of ligands. The double-barreled pipette with its protruding droplet enables operation in air, the biomolecule molecules may be dry to various extents. They can then be dissolved or resuspended as the protruding droplet comes atop. This is advantageous for making a simpler measurement system that does not require the sample to be wetted in advance, for example for forensic purposes at the scene of a crime, the nanopipette device can be passed over a surface at which a trace levels of a biospecimen may be present.

In some embodiments a double-barreled pipette, or an extra pipette is used. In some embodiments, the polymer does not enter one of the barrels or the extra pipette, instead they are used to measure reference ion flow. In some embodiments, the reference ion flow is used to determine the distance of the nanopipettes from the surface. A greater ion flow is obtained at greater distances from the surface and becomes increasingly reduced as the pipette approaches the surface. The barrel or pipette into which the polymer has entered and thereby partially blocked the ion flow, may have a reduced capacity to determine distance from the surface, for which the other barrel or extra pipette can be used. In the case of an array of pipettes, individual pipettes into which polymers have not entered can be used as reference pipettes.

In some embodiments the nanopipette comprises an orifice whose inner bore diameter at its narrowest part approximates close to the width of polymer(s) under analysis. In some applications it is preferable that the narrowest part is just sufficient to fit the polymer. However, a wider inner diameter (e.g., within 1-2 orders of magnitude of the width of the polymer) is appropriate for certain applications of the disclosure.

The nanopipettes, can form part of an array of nanopipettes and in this case need not be restricted to pulled glass capillaries but can be monolithic, nano or microfabricated structures.

The nanopipette orifice can be narrowed by coating with chemical or biological material (see also, Embedded Nanopores, below). An example of a biological material is Bovine Serum Albumin (BSA) (see also Embedded Nanopores, below). An example of a chemical material is polyacrylamide. The nanopipette may be coated with a functional layer or a passivation layer. The functional layer may serve to modify the properties of the nanopipetted surface. For example the surface property can be altered to facilitate interaction with specific substances e.g., for the formation of lipid bilayer. The passivation layer may comprise a lipid coating. It may also comprise a coating of BSA and/or Casein.

Although the aperture at the end of the nanopipette can be usefully deployed to make electrical measurements, particularly the change in ion flux as a polymer translocates through, with a typical aperture inner diameter of 50 nm it is difficult to obtain enough of a measurable change in ion flux, therefore a narrower pore at the end of the nanopipette can be included in embodiments preferred for certain applications (e.g., polynucleotide base sequencing and polypeptide amino acid sequencing).

Embedded Nanopores

In some embodiments of the present disclosure the nanopipette comprises one or more additional functional elements, preferably in proximity to the nanopipette orifice.

In some embodiments the inner diameter of the orifice is narrowed by one of a number of different functional elements. The following non-limiting examples illustrate some of the different types of elements that can be employed.

In some embodiments the pipette has a micro rather than a nano size orifice. Typically with an orifice size of 1-3 μm diameter. But a biological nanopore or ion channel can be embedded into pipette to produce a "nano" pipette.

Such nanopores can be chosen from *Mycobacterium smegmatis* porin A (MspA), alpha hemolysin, Phi 29 Packaging protein etc. To insert a biological pore at the pipette or nanopipette orifice or at some interior location of the nanopipette, a lipid bilayer that spans the orifice or the inner walls of the nanopipette is formed. Interaction of the nanopipette with Giant Unilammelar vesicles (GUVs) can be used to form bilayers at the nanopipette aperture.

A biological pore, such as MspA is allowed to spontaneously assemble in the lipid bilayer. Ionic current measurements can be used to characterize such treated nanopipettes before polymer analysis is conducted. Glass nanopipettes are also reusable; bilayers can be formed more than 50 times using the same glass nanopipette without cleaning. Bilayers formed by this approach are stable, even at high transmembrane voltages of a few hundred millivolts, enabling long-term recordings lasting several hours. After addition of GUVs to the system, a bilayer can be formed within seconds, producing high-resolution ion-current recordings, with typical seal resistances of 140 GΩ. Each lipid bilayer seal can be broken by applying a positive pressure to the back of the pipet using the attached syringe, some requiring applying a voltage of up to 1.3 V in addition. It is important to note, that the bilayer can then be easily re-formed by applying a negative pressure to draw another vesicle to the tip of the pipet.

Alternatively, artificially constructed nanopores such as a DNA nanostructure or DNA origami nanopore can be inserted inside the nanopipette orifice or form a structure that straddles the outside or both the inside and outside of the nanopores. The precise design control of DNA nanostructures/origami allows pores of arbitrary dimensions and structure to be constructed, with precisely located functional motifs. FRET Donors and acceptors or a donor and a quencher can be embedded in the DNA origami or nanostructure by using modified oligonucleotides. Streptavidin/neutravidin coated metal, latex or Quantum Dot particles can be attached by using biotin modified oligonucleotides to which streptavidin or neutravidin interacts. Alternatively, an intercalator dye can be incorporated at many locations in a DNA structure.

Furthermore, the additional nanopores may comprise micro or nanofabricated nanopores, nanogaps or nanotubes. They may also comprise carbon nanotubes or perforated graphene layers, graphene nanoribbons (GNR) and Molybdenum Disulfide ($MBO_2$) sheets. These nanopores, nanogaps, nanotubes and perforated layers may be retrofitted into the pipette (in this case the pipette does not need to approach nanoscales at its tapered end). Alternatively, a nanopipette can be fabricated from ground-up integrating nanopores or nanogap structures. Fabrication from the ground-up may use methods of the semiconductor industry, and may enable different materials to be combined as appropriate. For example, metals may be integrated to form electrodes, plasmonic antennae for Raman signal enhancement or conduits for the purpose of metal-enhanced fluorescence. The pipette end may comprise multiple nanopores or perforations. This notwithstanding, preferably only one macromolecule is analyzed at a time with such a structure.

A patch clamp system can be used to analyse individual polymers. In this case, a nanopores is not integrated into a nanopipette beforehand, rather the nanopipette forms an interaction with a nanopore already embedded in a membrane. This pore may be on a cell membrane or a mitochondrial membrane, for example.

Embedded Sensors

In some embodiments the nanopipette comprises a sensor. In some embodiments the sensor comprises one or more proteins, multimeric proteins or protein complexes. Such sensors may for example comprise a voltage-gated ion channel or a redox protein or complex. Such sensor may also comprise a fluorogenic sensor. Such fluorogenic sensor may comprise FRET donor and acceptor pairs. A measurable quantity of the sensor can change depending on the physicochemical properties or molecular structures in its close proximity. As a heterogeneous polymer translocates through the nanopipette different units of the polymer (e.g., DNA bases) come in proximity of the sensor and elicit a different measurable response of the sensor. For example if the sensor comprises a coupling of donor and acceptor, the different units (amino acids, or labels thereon) and their different molecular structures perturb the efficiency of the FRET interaction to different degrees, characteristic of the molecular structures.

Polymers Preferably the macromolecules comprise polymers or have an elongated chain-like structure. The nanopipette dips into, or is contained within, a solution comprising the polymers and interacts with one polymer at a time. Physical recordings are made as each polymer translocates into and through an individual nanopipette and as it interacts with the nanopipette and/or the surrounding medium. For example, ionic current is measured simultaneously with translation of the linear length of the polymer with respect to the nanopipette orifice. The physical recordings can be converted into chemically/biochemically relevant data preferably by reference to a look-up table.

The DNA can be extracted using a magnetic bead method and the pore then interacts with a free end of the DNA while the magnetic bead is used to hold the DNA in place. The magnetic beads can be attracted to a planar surface according to an electric field.

A main advantage of the approach is that the nanopipette/nanopore can be taken to the polymer and does not need to wait for the slower process of the polymer having to find the orifice. This is particularly useful when there is a small amount of material, e.g., from a small number of cells or from a single cell. The location of polymers on the surface can be pre-determined or pre-detected therefore it is easy for the nanopipette/pore to be directed to the polymers. The nanopipette can be coated with substances that attract the polymer. In the case where a lipid bilayer spans the nanopipette, a lipophilic or cholesterol tag can be attached to the end of the polymer. The end of nanopipette can be structured such that the entropic penalty for entering the small orifice is reduced. The structure can be a taper or funnel that approaches the constriction. In this case the nanopipette or at least the leading end of the nanopipette may be micro- or nano-fabricated.

The polymers can be embedded in a gel. The polymer can be extracted in a gel. Alternatively, the polymer is not pre-extracted from a cell but the polymer is sucked out of the cell using the nanopipette. As the polymer is sucked out of the cell, the features along the length of polymer can be detected. Alternatively, the polymer is sucked in first and then the features along its length are detected as the polymer is ejected.

Preferably the polymer is a polynucleotide or polypeptide. The polynucleotide may be double or single stranded and this will affect the choice of nanopipette constriction or nanopores opening. The polynucleotide may be DNA, RNA (e.g., microRNA, mRNA).

Immobilization

A part of the polymer or preferably one end of the polymer is immobilized. Preferably this immobilization is due to attachment to a surface. However, the immobilization can be by other means too, such as optical trapping. In the embodiments where the macromolecules are disposed on a surface and preferably a part of each macromolecule retains contact with a surface over the period of analysis while another part is relatively unconstrained and able to interact with the nanopipette. The polymers can form a random or ordered array on a surface. The surface may be a planar surface or it may be a 2-D crystal lattice formed for example, by DNA origami. Typically the surface is a planar surface and the nanopipette is perpendicular to or at an angle to the surface. The surface attachment may also be to a non-planar surface that the nanopipette is able to negotiate. A polynucleotide can be attached to the surface via one end. This can be done with or without modifying the end of the DNA. For example the latter can be achieved by exposing genomic molecule (e.g., a lambda phage) to a surface coated with an aminosilane and a high ionic strength buffer, e.g., 4×SSC. The end of a polypeptide can be attached to a NHS-ester coated surface.

One of the electrodes can be the surface on which the polymer is attached. For example, a gold surface to which the polymer is attached may be an electrode. A target polynucleotide can be attached to gold by hybridizing a thiol containing oligonucleotide (thiols interact with Gold) to the polynucleotide. Proteins/polypeptides can be attached via cysteines, lysines, the N-terminus etc. This set-up has the advantage that when the negative bias is applied to the surface, it not only serves as the electrode to induce ion flow, it also repels the negatively charged polynucleotide (or other polymer according its charge and the bias at the electrode), so that it moves away from the surface, while its surface tethered region remains attached. When the pipette contains a positive electrode a negatively charged polynucleotide can enter into the bore of the pipette.

In some embodiments the sample polymer is encased/embedded in a medium that preserves its long length. Such a medium can be a natural medium (e.g., cell or organelle). Such a medium can be an artificial medium (e.g., hydrogel, micro or nanofluidic channel/cavity). A number of repair enzymes can be included in the medium to repair DNA damage or nicks (which can lead to double-strand breakage) so that the long length of the DNA can be preserved.

In the case of folded polymers, such as proteins and RNA, the polymers are unfolded before analysis or during analysis. This can be done for RNA by having a denaturing environment comprising low salt concentration, urea, and/or formamide. If an end of a protein has a highly negative charged length (e.g., by grafting or engineering negatively charged amino acids or an oligo-/poly-nucleotide to its end), the negatively charged part can be attracted to a positively biased electrode inside the nanopipette and such a pulling force may be exerted on the polypeptide that it becomes unfolded and enters into the nanopipette. This can be facilitated by having the polypeptide in a denaturing environment containing guanidimium hydrochloride, urea, sodium dodecyl sulfate etc. Alternatively an enzyme with an unfoldase activity e.g., the chaperonin, ClpX can be used to unfold the polypeptide. Operating at elevated temperatures can also facilitate unfolding.

Molecular Array

In a related aspect, the disclosure concerns an array (the making of and the array itself) where molecules are configured on a surface in a such a way that in the majority of cases only individual molecules are sucked into the nanopipette orifice at any one time. This aspect of the disclosure requires a density of molecules on a surface which is conducive to one-molecule-per-nanopipette at-a-time analysis. It also requires the molecules on the surface to be presented in a way that they can be sucked up by the nanopipette. This requires the molecules to have a free end (not attached to the surface) and sufficient strand length that is unconstrained by interaction with a surface. In some embodiments, typically the density of molecules is >50 nm apart for a nanopipette comprising a 50 nm orifice. The density can be higher when for example a nanopipette contains a nanopore, which constricts the opening further. In some embodiments, typically the length of molecule that is unconstrained is >100 bases or base pairs. Such factors can be determined empirically.

The surface attachment of the target biomolecules overcomes the problem of multiple molecules entering the pore simultaneously, by choosing the density of the surface bound molecules such that molecules can be addressed individually. For example, surface bound molecules can be provided in a spatially addressable microarray, where different elements of the array (e.g. microarray spots) contain different surface bound species, and each element contains a plurality of the surface bound species.

Physical Control of the Polymer and its Translocation into the Nanopipette

When an electrical potential (voltage or bias) is applied between the two electrodes, an ionic current can flow. When the polymer is a cationic polymer (e.g., DNA) and is approached by the nanopipette which contains the anodic electrode, the polymer is attracted by the nanopipette and its motions can be reduced. The polymer's movement can be controlled by the nanopipette and it can be pulled away from the surface while remaining anchored by the part that is in contact with the surface. When the nanopipette is close enough to the surface, and the polymer has been attracted close to the nanopipette the polymer can enter into the nanopipette orifice. After entering the nanopipette orifice the polymer can be sucked into the nanopipette, such that a substantial length of the polymer comes to be inside the nanopipette; due to the ionic flow and the anodic electrode at the nanopipette end opposite the orifice, the DNA polymer can be extended or stretched along the longitudinal axis of the nanopipette.

Polynucleotides (e.g., DNA) with their negatively charged backbone can enter into the nanopipette through an electrophoretic effect as only the inside of the nanopipette (or one of the bores in the case of a double-barreled nanopipette) contains the positive electrode to which it is attracted. In this way the DNA can be sucked up inside the nanopipette.

The polymer moves into the nanopipette in a way that can be compared to sucking up spaghetti or noodles.

In some embodiments the "sucking" of the polymer by the nanopipette is a passive process caused by capillary forces acting on the polymer. In some embodiments the sucking is an active process. Polymers can be actively sucked into the nanopipette by suction applied to the top of the nanopipette which pulls the liquid through the orifice. In another embodiment pressure is applied on the fluid outside the nanopipette and this is at a higher pressure than at the top end of the nanopipette. This induces fluid flow with which DNA becomes elongated inside the nanopipette.

The solution on the outside of the nanopipette can be contained in a channel or slit. A positive pressure can be applied atop the solution at an inlet to the channel or slit. The back end of the nanopipette can comprise a second outlet which has a negative pressure with respect to the inlet in the channel or slit. This serves to elongate the polymer inside the nanopipette by pressure driven flow. The elongation of the polymer can be due to hydrodynamic forces that are exerted on the polymer. In another case there is a voltage bias applied between the exterior and interior of the nanopipette which causes an ionic current to flow, which serves to move polymers, electrophoretically depending on their charge and the polarity of the voltage.

The DNA end once in the nanopipette can become attached inside the nanopipette. Specific attachments sites can be provided inside the nanopipette.

Due to the electric field the polymer (if it bears the appropriate charge or charge distribution) can become elongated towards the nanopipette when the nanopipette approaches the polymer.

When the polymer is elongated or stretched towards the nanopipette its random coil nature is reduced or substantially eliminated and it becomes rod-like with a long persistence length, and the speed of the translocation through the nanopipette orifice can be purely or largely due to the z-direction translation of the surface with respect to the nanopipette (or vice versa).

In some embodiments the polymer is first sucked up inside of the nanopipette and measurements are made as it is released. The nanopipette/surface is translated in the z direction (assuming the sample surface is held in the horizontal plane) and once the polymer (or part of the polymer) has been sucked inside, any change in ionic current is detected as the polynucleotide translocates out due to the z movements. The z direction translation can be a back and forth translation.

Long-Range Analysis

The length of the nanopipette is several tens of centimeters which is longer than the longest human chromosome, which is 7.35 cm assuming a separation of 0.34 Angstrom between DNA bases as seen in the double helix crystallographic structure. In some cases DNA is stretched to its crystallographic length or beyond.

The nanopipette can be translated up and down in the perpendicular axis with respect to the surface. As the nanopipette is translated up and down the longitudinal length of the polymer which is elongated towards the electrode inside the nanopipette is translated with respect to the nanopipette orifice.

Ideally, substantial lengths of the polymer are analyzed. The lengths that can be monitored would depend on the translation range of the nanopipette with respect to the surface. Contributions to the translation range can come from movement of the nanopipette and movement of the surface. As an alternative to the need for translation of the nanopipette over the length of an extended polymer, the polymer can be bundled on the surface and then sucked in without further movement of the nanopipette. Once it has passed the constriction the polymer it can become bundled up again. If the internal dimensions of the nanopipette are large enough a large length of the polymer inside the nanopipette will not substantially affect the ionic current.

Physical Recordings

In some embodiments the physical recordings are electrical recordings. For example, the nanopipette is used as part of an electrical/electrochemical sensing circuit.

The conductance of ion channels is minute, comprising a current measured in pico-amperes (one trillionth of an Amp). The signal has to be amplified and the noise kept as low as possible.

In other embodiments the physical recordings are optical recordings. For example the Fluorescence resonance energy transfer (FRET) between a donor and acceptor, is measured. In some embodiments both electrical and optical recordings are utilized. For example, electrical recordings are made of the ionic current flux as the polymer translocates into or out of the nanopipette, while far field optical measurements are made as the stained DNA becomes elongated away from the surface due to its interaction with the nanopipette. The optical signal detected goes from that of a highly fluorescent blob to a less fluorescent point source, as the majority of the stained polymer is lifted away from the surface.

In some embodiments the solution is contained in a vessel comprising an electrical contact or electrode.

In the case of an optical sensor, such as one comprising a donor-acceptor system, the readout is optical and can be made through distal optical sensors such as photomultiplier tube or avalanche photodiode or a Complementary metal-oxide-semiconductor (CMOS) device which are focused at the location of the optical emitters through an objective lens. Use of a charge-coupled device (CCD) or 2-D array CMOS detector is compatible with analyzing an array of optical nanopipette sensors. In the case of such a method which requires focusing to obtained, it is preferable that the surface to which the polymer is attached is translated in the z direction rather than the nanopipette which is held in place so that focus can be maintained on events in the proximity of the nanopipette constriction.

In preferred embodiments an ionic current is measured simultaneously with translation, of the linear length of the polymer with respect to the nanopipette orifice.

The electrical signals are preferably converted into meaningful chemical/biochemical data. The conversion can occur by reference to a look-up table. Signal processing can be used to extract information from the electrical signals which may be noisy.

A number of alternatives to correlating electrical signal with distance of nanopipette from a surface can be used. If the rate of translocation of the polymer is known and is fairly constant, the time from first blockade event can used to correlate electrical signals to distance from the end of the molecule. A difference in capacitance inside the nanopipette can be measured to indicate the length of the polymer that is inside the nanopipette (hence location). If the polymer strand is fluorescently labeled (e.g., with an intercalator dye in the case of double stranded DNA or Sypro Ruby in the case of a polypeptide), the fluorescence intensity inside the nanopipette can be measured. Only the length of polymer inside the nanopipette can be illuminated by using a local light source or a light guide or evanescent waveguide to illuminate the inside of the nanopipette.

As the real-time signals are monitored a pattern of features such as a sequence motif (e.g., a repetitive DNA sequence), can be detected, that may cause an action to be taken, such an action can be the analysis of the polymer (or part of it) more closely by slowing down the up and down movement of the nanopipette. The action can also be to add reagents to the polymer or to conduct some physicochemical process on the polymer, e.g., light induced cleavage in the region of a specific recognition site.

In some embodiments a voltage waveform is applied, for example an oscillatory waveform is applied. This can aid the translocation of the polymer and can facilitate measurements.

In some embodiments the location of units of a heterogeneous polymer do not need to be determined, only their consecutive order needs to be determined.

The nanopipette can suck in one or more polymers from polymers not attached to a surface. Measurements can then be made on each of the polymers as they are individually ejected from the nanopipette. The nanopipette may move to an area containing a surface onto which the ejected polymer can stick. In this way an end of the polymer is ejected, that end sticks to the surface, the nanopipette is moved away from the surface as more of the polymer is ejected, and physicochemical recordings are made as the polymer translocates out of the nanopipette (or repetitively moved in and out of the nanopipette). Hence, the nanopipette can suck out DNA, RNA or a polypeptide from a cell, and then move to an appropriate location, eject some portion of the DNA, RNA or polypeptide so that parts of individual molecules stick to a surface and then can be analysed by sucking back into the nanopipette.

In other embodiments the nanopipette can analyse biopolymers that are inside cells by piercing the cells and sucking out the biopolymers from inside the cell. The nanopipette can analyze the polymer while it is being pulled out of the cell. In the case of proteins the nanopipette can interact with cellular protein transportation systems, which retain or render proteins in a polypeptide form.

Sequencing a Complete and Sub-Set Inventories

In some embodiments the disclosure is a method for sequencing of a complete inventory. For example, this may be RNA (e.g., mRNA, microRNA etc.) from a single organelle, cell, tissue or organism or from a population of such. It may also be a compete genome from a single chromosome, organelle (e.g., mitochondria, nucleus) cell, tissue or organism.

Genomes of single-cell and higher organisms are organized in chromosomes. In human whole chromosomes, and the length of a single DNA can be several centimeters in length. The method can be applied to molecules of exceedingly long lengths, and is only limited by the length of the target DNA molecule that can be kept intact; the range of the z movements can several centimeters, surpass the length of the longest human chromosome.

The sequencing may be of a selected sub-set. For example, certain sequences may be chosen for analysis. This may be achieved by selecting the molecules of interest (e.g., by PCR, Agilent Sureselect or Halo) prior to immobilizing the sample polymers. It may also be achieved by rendering on the surface capture probes for the sequences of interest. These capture probes may be organized randomly on a surface. For example, a large set of oligonucleotide probes can be synthesized on a microarray, cleaved from the microarray, amplified and then attached to the surface. The capture probes may also organized on a surface as a microarray. Such a microarray can be synthesized by light directed methods (e.g., by vendors such as Affymetrix, Nimblegon/Roche, LC Sciences, Mycroarray, Flexgen), by ink-jet synthesis (e.g., Agilent, Oxford Gene Technology) or electrochemical deprotection (Custom Array). Microarrays can also be spotted either in-house or using companies such as ArrayJet or Arrayit.

The subset of polymers may also be chosen by isolating specific chromosomes and immobilizing the DNA from the isolated chromosomes. The whole length of DNA extracted from a single chromosome can be disposed for analysis. Alternatively, the chromosomal DNA is rendered into sub-fragments which are disposed on a surface for analysis.

When arrayed randomly, the concentration and immobilization conditions of probes can be controlled to give a desired density. When a microarray is produced, a low density of probes within each spot can be produced directly, or by density reduction after microarray production. A regular density microarray can also be produced and the capture efficiency can be manipulated to capture the desired density of target polymers. As the capture may not be 100% efficient, a higher density of probes may be attached to the surface than expected to be captured. The capture efficacy may be from 1-99% and can be determined empirically for any given system. Initially In such empirical determination can start with an assumption of a capture efficiency of 10% and then after measurements are made, the concentration can be adjusted.

As well as being capture probes, arrayed polymers may themselves be the target polymers for nanopipette analysis. For example, it may be desirable to analyse a portion of molecules in a microarray to sample array synthesis efficiency and fidelity.

Mapping and Sequencing by Oligonucleotide Binding

Oligonucleotides (oligos) can be hybridized to the polynucleotide polymer prior to nanopipette analysis. The nanopipette analysis will then detect which oligos have been bound and their locations of binding along the DNA polymer. If individual oligos are used one at a time, no labels need to be attached to the oligos. If more than one oligonucleotide is used, they can be differentiated by tags that produce differentiable signals in the nanopores analysis.

Alternatively, the nanopipette can deliver the oligos to an individual polynucleotide strand under conditions that they will bind to the polynucleotide in a substantially sequence specific manner. The advantage of this is that different oligos or oligo sets can be delivered to different polynucleotides and that very small quantities of oligos are used up; the oligos can be released when the DNA molecule has been brought into the nanopipette, so the hybridization volume will be tiny.

In this way the structure of a polynucleotide can be examined by obtaining a map of the oligo binding along the polynucleotide. Taken to its logical conclusion if a complete repertoire of oligos is bound to the polynucleotides in a sequence specific manner, the sequence of the polynucleotide can be determined. The binding would not be expected to be limited to only the perfect match, the occurrence of a range of mismatches need to be taken into account. An algorithm is used to assemble the sequence; a number of existing de novo assembly or sequencing-by-hybridization algorithms can be used as the basis of the algorithms. In practice the repertoire may or not be substantially complete and gaps may remain in the sequence but sufficient information will be obtained to assign a sequence in combination with a reference genome.

As such molecular interactions are stochastic, some locations may not bind in a given time frame. But the oligos can be denatured from the DNA and applied again under the same conditions or under different conditions. Different condition may comprise different temperatures, buffers, electrolyte concentrations etc.

The sequence may be de novo assembled or assembled based on a reference. In practice a combination of the two approaches may be used. In cases where gaps exist, the sequence at the reference genome can be used to predict the sequence in the gaps.

Deposition and In Situ Synthesis

In some embodiments the back end of the nanopipette is in fluidic contact with another fluidic vessel, for example a channel for fluid delivery.

The nanopipette can also be used to deposit the sample molecules, multiple at a time at each location or one at a time at each location. This can allow sample molecules to form an ordered array, by moving the nanopipette a fixed distance before each subsequent deposition. After deposition the nanopipette can be used to check the sample molecule has been deposited or has become localized at the surface or perform analysis on the polymer.

The nanopipette or a plurality of nanopipettes can be used to perform in situ synthesis of a polymer on a surface by delivering monomers (phosphoramidites in the case of DNA synthesis) and various other reagents. Alternatively other reagents are delivered by flooding the whole surface. Hence, the nanopipette delivery is restricted to the selective delivery of monomers to different locations on a surface and flooding is used to deliver the common reagents. In this way a library of polymers can be made (with different locations comprising polymers of different sequence). This can be done much like existing ink-jet synthesis methods. An array containing different biopolymers at different locations can be created by such a method. A good reason for wanting to do this is, that following synthesis or during synthesis, a nanopipette can be used to determine if the correct base is added, the yield of the synthesis or if any damage has occurred, e.g., depurination. This can lead to the synthesis of high fidelity oligonucleotides, which are important for emerging synthetic biology approaches.

Detecting Physical Properties

The physically properties that can be measured directly are for example e.g., the electrical permittivity of the sub-unit resident at a particular location in the nanopipette (e.g., at the narrowest part, whether that is defined by the nanopipette itself or an integrated nanopore). The physical property can be measured indirectly, for example, particular physical properties (e.g., size, charge, hydrophobicity etc.) can have an effect on the ionic current flow through the narrowest part.

Repeated Readings

In some embodiments, physical recordings are made as the nanopipette is translated up and down with respect to the longitudinal axis of the polymer. This repetition can be used to improve the accuracy of the measurement obtained for each longitudinal location on the polymer. The range of the repetition can be controlled on the fly, if a reading from a particular part of the DNA is ambiguous, then that part of the DNA can be analyzed again. Hence feedback from a base calling algorithm can instruct the instrument control mechanism.

In some embodiments the nanopipette or nanopore is not translated but the polymer can be wound back and forth. DNA may be wound as a nanoball and may be the product of rolling circle amplification. When not attached to a surface the polymer can be constrained by optical, magnetic or electrical traps; labels (e.g., magnetic nanoparticles or beads) can be added to the polymer to facilitate this. The polymer can be pulled in our out of the nanopipette by a molecular motor. Such a motor may comprise a helicase (e.g., XPD), a polymerase (e.g., Phi29) for DNA or a chaperone protein (e.g., ClpX) which can translocate proteins. The molecular motor itself may be the pore that is integrated into the nanopipette (e.g., ClpX, Phi29 packaging protein).

Moving on to the Next Polymer in the Array

Once the polymer has been inside the nanopipette and after sufficient recordings along the length of the polymer have been made the polymer can be ejected from the nanopipette. After analyzing a first polymer the nanopipette can dissociate from the polymer and analyse a second polymer, and then a third and so on. An array of nanopipettes can be provided so that an array of polymers can be analyzed substantially simultaneously.

Much as what has been described for polymers can be applied to other chain-like macromolecules or supramolecular complexes. The methods described in this disclosure can be applied to when there is nanopipette with no integrated nanopores or when a nanopores is integrated with the micropipette or nanopipette even where this is not explicitly stated in the above text.

Instrument

The instrument of this disclosure comprises a holder for the sample substrate (or device as described below) which is mounted on an XYZ stage. A nanopipette is mounted above the substrate in an immobile position via a holder. In some embodiments the sample substrate is mounted on a fixed holder (no movements in X, Y, or Z directions) and the holder for the nanopipette is attached to a device for X, Y, Z movements. In some embodiments the nanopipettes contains an electrode. In some embodiments the instrument contains a head-stage for the electrode which is connected to an amplifier. In some embodiments the electrodes are connected to a waveform generator. In some embodiments the electrodes are connected to a voltage power source. In some embodiments the instrument comprises a fiber optic source which is connectable to the back of the pipette. In some embodiments the instrument comprises a laser or Light emitting diode (LED) attached to the fiber optic source or coupled into the substrate (e.g., via total internal reflection (TIRF).

In some embodiments an electrode is provided to dip into the electrolyte within the device described below. In some embodiments the instrument provides electrical interface to the electrode. One electrical connection is made to the electrolyte on the substrate and another to the electrolyte in the pipette, so that a potential difference can be created in the continuous fluidic connection between the electrolyte on the substrate and the electrolyte in the pipette. In some embodiments and optical microscope is provided at the other side of the substrate than the nanopipette. In some embodiment optical microscope is provided to provide illumination light and to collect light. In some embodiments the optical microscope is provided solely to collect light (e.g., when the illumination is via fiber optic inserted into the back to the pipette or when light is provided via another source). The optical microscope comprises a lens (e.g., a high NA, air, water or oil immersion objective lens, optical filters to select or reject light, dichroic filters, prisms, mirrors, means to move the components in relation to each other and a detector such as a CCD or CMOS camera. In some embodiments the instrument comprises an on board computer. In some embodiments the instrument comprises a field-programmable gate array (FPGA). In some embodiments the instrument comprises a user interface. In some embodiments the user interface is a monitor such as touch sensitive LED display.

In some embodiments these components are housed in a faraday cage. In some embodiments the components are mounted or placed on an anti-vibration surface, which may be active or passive.

In some embodiments instrument essentially comprises a Scanning Ion Conductance Microscope (SICM) (P. K. Hansma, B. Drake, O. Marti, S. A. Gould and C. B. Prater, Science 243, 641 (1989)) to which consumable pipettes are attached and which contains a holder for the consumable substrate onto which the molecules or cells under analysis are attached. The basic features of the SICM that are used in some embodiments are XYZ movement of the substrate and connection of the nanopipette to a head-stage and an amplifier. In some embodiments the SICM functionality of the instrument is used to monitor and control (via feedback loop) the distance of the nanopipette from the substrate. In addition to the SICM functionality of the instrument, the instrument additionally comprises a functionality for measuring features along the polymers or chain-like macromolecules or complexes. In some embodiments electrode(s) within the nanopipette are used to detect the features. In some embodiments, far field optical detectors are used to detect features. In some embodiments the ionic current detection part of the instrument (e.g., the SICM part) is associated with an optical illumination and detection part. Such optical part of the device comprise a light source (e.g., a 488 nm blue laser) an objective lens, a detector (such as a CCD camera), filters, mirrors and relay lenses and in some embodiments a fiber-optic coupled from the light source to the back of the nanopipette. In some embodiments the optical measurements are made with an inverted optical microscope onto which the SICM is mounted. In some embodiments the instrument comprises a computer and/or a Field Programmable Gate Array (FPGA).

Device

Some aspects of the disclosure comprise a device on which the samples are loaded, attached and where the analysis takes place as the nanopipettes of this disclosure interact with the molecules under analysis. The device comprises an opening for loading the samples, and exchange of fluids. It contains a barrier to confine and contain fluids such as the electrolyte solution and it contains an opening so that the nanopipettes can access the molecules under analysis. In some embodiments an electrode is provided within the barrier area.

In some embodiments the nanopipette is the device, or is a consumable part of the instrument. In some embodiments the nanopipette device contains functional components such as electrodes or biomolecules.

Computer Implementations

It should be appreciated that methods disclosed herein may be implemented in any of numerous ways. For example, certain embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a smart phone, tablet, or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools (e.g., MATLAB), and also may be compiled as executable machine language code or intermediate code that is executed on a framework or virtual machine.

In this respect, aspects of the disclosure may be embodied as a computer readable medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other non-transitory, tangible computer storage medium) encoded with information (e.g., sequence information) and/or one or more programs that, when executed on one or more computers or other processors, perform methods that implement the various embodiments of the disclosure discussed above. The computer readable medium or media can be transportable, such that the program or programs stored thereon can be loaded onto one or more different computers or other processors to implement various aspects of the present disclosure as discussed above. As used herein, the term "non-transitory computer-readable storage medium" encompasses only a computer-readable medium that can be considered to be a manufacture (e.g., article of manufacture) or a machine.

The terms "program" or "software" are used herein in a generic sense to refer to any type of computer code or set of computer-executable instructions that can be employed to program a computer or other processor to implement various aspects of the present disclosure as discussed above. Additionally, it should be appreciated that according to one aspect of this embodiment, one or more computer programs that when executed perform methods of the present disclosure need not reside on a single computer or processor, but may be distributed in a modular fashion amongst a number of different computers or processors to implement various aspects of the present disclosure.

As used herein, the term "database" generally refers to a collection of data arranged for ease and speed of search and retrieval. Further, a database typically comprises logical and physical data structures. Those skilled in the art will recognize methods described herein may be used with any type of database including a relational database, an object-relational database and an XML-based database, where XML stands for "eXtensible-Markup-Language". For example, sequence information may be stored in and retrieved from a database.

Computer-executable instructions may be in many forms, such as program modules, executed by one or more computers or other devices. Generally, program modules include routines, programs, objects, components, data structures, etc. that perform particular tasks (e.g., tasks relating to Feedback control) or implement particular abstract data types. Typically the functionality of the program modules may be combined or distributed as desired in various embodiments.

EXAMPLES

Quartz Nanopipette Fabrication

In some embodiments, nanopipettes are fabricated from quartz capillaries with filaments, with an outer diameter of 1.0 mm and an inner diameter of 0.70 mm (QF100-70-5; Suffer Instrument Co.). In some embodiments, the capillary are pulled using a P-2000 laser puller (Suffer Instrument Co.) preprogrammed to fabricate nanopipettes with an inner diameter of approximately 50 nm. Parameters used are: Heat 625, Filament 4, Velocity 60, Delay 170, and Pull 180. In some embodiments, a solution of 10 mM buffer and 100 mM KCl, the pipettes give a current between −2500 and −4000 pA at a potential of −0.5 V.

Measurement Setup

In some embodiments, for measuring ionic current through a nanopipette, a two electrode setup is used. In some embodiments, a nanopipette is backfilled with buffer solution and an Ag/AgCl electrode inserted. In some embodiments, another Ag/AgCl electrode is placed in 0.3 mL bulk solution acting as auxiliary/reference electrode. In some embodiments, one or both electrodes are connected to an Axopatch 700B amplifier with the DigiData 1322A digitizer (Molecular Devices), and a PC equipped with pClamp 10 software (Molecular Devices). In some embodiments, positive potential refers to anodic potential applied to the electrode in the barrel of the pipette relative to the counter electrode. In some embodiments, experiments are carried out at 24° C.

In some embodiments, the nanopipette comprises a filament inside its interior (which facilitates the drawing in of solution).

The instrument can have feedback control which sets the distance from the surface and prevents the nanopipette from crashing to the surface, and any other measures implemented in Scanning Ion Conductance Microscopy (SICM).

DNA can be attached at one end can be stretched by providing an electric field for example, 15 volts per cm.

AG/AgCl electrodes can be prepared by chlorination of bare silver wires in a 1M KCL solution at 1.5V for 20 s. The electrode wire is inserted into the back of the nanopipette.

The nanopipette is attached to an amplifier head-stage. The nanopipette is placed inside a liquid and is placed in an evacuated chamber, which allows the liquid to be drawn into the nanopipette.

The nanopipette can be operated in two modes. In direct current (DC) mode (constant distance mode), the micro-pipette is lowered toward the sample until a predefined resistance is reached. The pipette is then moved laterally and a feedback loop maintains the distance to the sample (through the resistance value). In alternating current (AC) mode, the micro-pipette oscillates vertically in addition to its usual movement.

To form an artificial bilayer, the pipet tip is carefully apposed to the surface of a GUV, which is anchored to a surface, using a micromanipulator and gentle suction is applied to the back of the pipet to form a seal. The pipet must be carefully withdrawn from the surface of the GUV, quickly passing the tip through an air/water interface if necessary. The stability of lipid layers formed in nanopipettes is better than traditionally built bilayers supported in Teflon membranes, for example their lifetimes are longer and they can be made in minutes without a clean room.

Instrumentation

A SICM bought from Ionscope (Melbourn, Cambridgeshire, UK) can be used. The SICM can be deployed atop an inverted microscope such Nikon Ti-E, so that joint ionic and fluorescent measurements can be made. In some embodiments optical or fluorescent measurements may be used just to locate the target molecules on the surface, and in some embodiments the ionic current measurements may be used just to determine the distance of the nanopipette from the surface. In some embodiments the optical or fluorescence measurements may be used for interrogation of the features of the molecules on the surface. In some embodiments the ionic measurements are used for interrogation of the features of the molecules on the surface.

With a static nanopipette the following XYZ control devices from Physik Instrument (Karlsruhe, Germany) can be used to conduct up and down motions of the surface with respect to the nanopipette, in order to traverse along the polymer and the X and Y can be used to move from one polymer molecule to another:

P-620.ZCL Precise PIHera Vertical Nanopositioning Stage, 50 µm, Capacitive Sensor, LEMO Connector(s)

P-620.2CL Precise PIHera XY Nanopositioning System, 50 µm×50 µm, Direct Metrology, Capacitive Sensors, LEMO Connector(s)

E-725.3CDA Digital Multi-Channel Piezo Controller, 3-Channel, Sub-D Connector(s) for Capacitive Sensors, Analog Inputs P-895.3LDC Adapter Cable, Sub-D 7W2 (f) to LEMO Connectors (m) for Piezo-Actuator-Based Nanopositioning Systems with Capacitive Sensors, 3 Channels, 0.3 m Embedded Nanopore-Nanopipette The nanopores-nanopipette is formed essentially as described in Gornall et al. NanoLetters 2011, 11, p 3334 (which in its entirety is incorporated by reference). Borosilicate glass capillaries (Hilgenberg GmbH, Germany), with an outer diameter of 0.5 mm and a wall thickness of 0.064 mm are used. Pipets are prepared by drawing the glass capillaries with a laser pipet puller (P-2000, Sutter Instruments). Prior to use, the capillaries are thoroughly cleaned by sonicating in acetone and ethanol for 5 min. Residual ethanol from the cleaning process is removed with gaseous nitrogen. Following cleaning, the capillary is mounted in the laser pipet puller where the glass is heated and pulled to form two virtually identical pipets. By tuning the parameters of the pull, such as temperature and velocity, nanopipettes with tip diameters between 230 and 785 nm are produced. In order to verify the shape and diameter of the tip, pipets are imaged using scanning electron microscopy (SEM). Prior to visualization in the SEM, the nanopipettes are coated with a 10 nm thick layer of palladium/gold (Pd/Au).

GUVs are prepared by electroformation in an indium tin oxide (ITO)-coated glass chamber connected to the Nanion Vesicle Prep Pro setup (Nanion Technologies, Munich, Germany). The ITO layers on the two glass slides are electrically conductive and therefore serve as electrodes. A 5 mM solution of 1,2-diphytanoyl-sn-glycero-3-phosphatidylcholine (DPhPC; Avanti Polar Lipids, Alabaster, Ala.) with 10% cholesterol in chloroform is deposited onto the ITO-coated slides, and the chamber is filled with a 1 M solution of sorbitol (Sigma-Aldrich) in ddH2O. Electroformation is controlled by the Vesicle Prep Pro setup, and all parameters for the electroformation are programmed in the Vesicle Control software (Nanion Technologies, Munich, Germany). Typical values of the amplitude, frequency, and duration of the potential applied across the chamber are 3 Vp-p, 5 Hz, and 2 h, respectively. Vesicle preparation is performed at 37° C. The formation of GUVs is highly reproducible and by adjusting the concentration of lipids used, GUVs can be formed with diameters in the range 1-100 µm. Typically, the diameter of the GUVs in solution required to form a bilayer on the glass pipet is between 5 and 50 µm.

Purified wild-type OmpF (1.5 mg/mL) in 1% n-octyl-polyoxyethylene (octyl-POE; Bachem, Bubendorf, Switzerland) is reconstituted into GUVs. The reconstitution of a single hydrophobic membrane protein is more complex than the reconstitution of water-soluble proteins. The protocol for micellar insertion of membrane proteins into lipid bilayers involves the removal of detergents. In the case of nanopipette supported lipid bilayers, addition of even small quantities of detergent leads to immediate disruption of the membrane. Therefore, following incubation of the GUVs with the porin solution, octyl-POE is removed using Bio-Beads (Bio-Rad, Munich, Germany). The mixture is incubated at 4° C. overnight, and the Bio-Beads are removed afterward by centrifugation. Direct insertion of membrane proteins into GUVs is challenging, and the protocol needs to be optimized for each individual protein due to the relative instability of GUVs. The average number of proteins in each GUV can be efficiently optimized by the varying protein concentration and the time of incubation. Proteo-GUVs were used directly for lipid bilayer formation, and when kept at 4° C., the proteo-GUVs could be used for over a week successfully. Since a-hemolysin is soluble in water, its incorporation into the lipid bilayer is achieved by adding the protein to the solution and mixing.

The experimental setup is based around a custom-built inverted microscope which allows the vesicles and nanopipette to be imaged during the experiment. Single-channel current measurements are performed using an Axopatch 200B amplifier (Axon Instruments, Foster City, Calif.) in voltage clamp mode. The signal is filtered using a four-pole low-pass Bessel filter at a frequency of 2 kHz and sampled at 10 kHz. The signals are acquired with a NI-PCIe-6251 card (National Instruments, USA), and data is recorded using custom written LabVIEW code. Pipets and the surrounding bath are filled with a buffer solution containing 150 mM KCl and 10 mM MES (pH 6). Chlorinated (Ag/AgCl) silver electrodes (200 µm diameter) are placed in the nanopipette and bath. Ag/AgCl electrodes are prepared by chlorination of bare silver wires in a 1 M KCl solution at 1.5 V for 20 s. For bilayer measurements the bath electrode is defined as the ground. The nanopipette is attached to the headstage (CV203BU, Axon Instruments) of the amplifier via an adaptor and attached to a micromanipulator (Patch-Star Micromanipulor, Scientifica). This allows for precise control of the nanopipette with an accuracy of 100 nm. Before each experiment, the electrode offset is set to zero, and the nanopipette is tested for stable current-voltage characteristics. In order to from a lipid bilayer, 10 µL of the vesicle solution is pipetted into the bath solution and a negative pressure of approximately 1 Pa is applied to the back of the nanopipette, using the attached syringe to draw the vesicles to the orifice of the nanopipette. When a vesicle come into contact with the tip of the capillary, it breaks and a bilayer with a high seal resistance formed immediately.

Optical Nanopipettes

An optical nanopipette is formed as described by Korchev et al Volume 78, Issue 5, May 2000, Pages 2675-2679 Biophysical Journal): This consists of a scanning probe, piezo-actuator scanning elements, control electronics, and a computer. These components are built in and around an inverted microscope.

Pipettes are fabricated by pulling borosilicate, glass microcapillaries with outer and inner diameters of 1.00 mm and 0.58 mm, respectively using a laser-based micropipette puller (Model P-2000, Sutter Instrument Co., San Rafael, Calif.). This reproducibly and easily produces probes with conical taper lengths and apex diameters of 200 nm, 400 nm, and 1.0 µm, respectively. The corresponding inner diameters are 100 nm, 200 nm, and 500 nm, respectively.

Three-dimensional and high-precision movement of the pipette relative to the sample is achieved by the piezo-translation stage (Tritor 100, Piezosystem Jena, Germany) on which the SICM pipette is mounted. The stage has a range of 100 µm in the x, y, and z directions so that scanning over biological samples with features that scale up to 30-50 µm is possible.

The pipette-sample separation is maintained at a constant value by monitoring the ion-current that flows between Ag/AgCl electrodes in the micropipette and electrolyte solution in which the sample is immersed. Phosphate-buffered saline (PBS) solution can be used for both filling the micropipette and the surrounding medium. The ion-current is measured for DC voltages of 50 mV applied to the electrodes. It is amplified by means of a high-impedance operational amplifier (OPA129, Burr Brown International, U.S.A.) and converted to a voltage signal over a resistance of 108Ω. This signal is then input into the control electronics where it is used for feedback control and data acquisition.

The micropipette is housed in a special, custom-made holder which is assembled together with the current amplifier and piezo-translation stage to comprise the SICM head. The SICM head is mounted onto a second z-translator on top of the inverted microscope that facilitates coarse vertical positioning of the micropipette relative to the sample immediately below it. The sample is contained in a petri dish placed on the microscope's stage. Movement of the sample relative to the micropipette is achieved by the x, y translation controls of the stage. The processes of monitoring the vertical position of the micropipette relative to the sample and selection of an area of interest on the sample can be viewed on a TV screen via a video camera (JVC TK-1280E, Victor Company, Japan).

Modifications are made to the set-up described above to permit simultaneous SICM and scanning near field optical microscopy (SNOM) imaging. Continuous wave laser light (Laser 2000 Ltd, UK of wavelength, 532 nm, is coupled via a multi-mode fiber (FG-200-UCR; 3M Specialty Optical Fibers, West Haven, U.S.A.) into the pipette. In order to confine light to the aperture, 100-150 nm of aluminum is evaporated onto the walls of the pipette. The scattered laser light is collected by a 60× long working distance objective and relayed by transfer optics onto a PMT (D-104-814, Photon Technology International, Surbiton, England) to record the optical signal. Simultaneous optical and ionic measurement of the sample are acquired using the control/data acquisition hardware and software produced by East Coast Scientific (Cambridge, UK).

A fast camera e.g., 4 Picos (Stanford Computer Optics) with a gate time down to 200 picoseconds can be used to make ultra-fast optical recording. The ImageEM from Hamamatsu can also be used. The optical recording can be via relay from a single nanopipette to a PMT or APD or CCD or CMOS. The optical recordings from multiple pipettes can be relayed to a CCD or CMOS.

Molecular Arrays

Arrays can be made in which the location of the molecule does not specify the identity of the molecule until the molecules are sequenced or an encoding is decoded.

This type of array is also characterised by the fact that single molecules of the same identity are not necessarily found in the same region but are arranged randomly e.g., Sequence A may be adjacent to Sequence B and a second occurrence of Sequence A may be at a distal location from the first occurrence. This random arrangement of the molecular species is due to the method used for making the array. Although having the molecules in such a random location does not confer any advantages, the fabrication of this type of array is far simpler than the fabrication of an array where many molecules of the same species are found in the same region on the surface as is the case for DNA colonies/Polonies or DNA microarrays.

For example a mix of an oligonucleotide complementary to the sticky ends of Lambda DNA (see below) each bearing a fluorescent label are pipetted at a concentration of 0.5 uM each in 50% DMSO onto APTES coated slides.

Linear Lambda DNA has complementary 12 base overhangs which allows it to be captured by complementary oligos on the array. The following oligonucleotides complementary to each end overhang are used in the following examples:

Lambda A:
(SEQ ID NO: 1)
5' GGG CGG CGA CCT 3'

Lambda B:
(SEQ ID NO: 2)
5' AGG TCG CCG CCC 3'

The oligos can be unmodified or modified with an amine or thiol group depending on what surface it is to be immobilised on. Amersham UV Crosslinking reagent (containing DMSO) was spotted with an equal volume of oligonucleotide dissolved in milliQ $H_2O$ was used to spot the probes onto an aminosilane modified slide (Asper, Estonia). After spotting, the slides were crosslinked at 300 mJoules of UV light followed by two washes in hot water followed immediately by drying by blowing with forced air from a pressurised airduster canister. The oligonucleotides were spotted at 5 uM and 500 nM concentrations (using spot diameter setting 255 microns, spots per dip: 72, 55% humidity on the Amersham Pharmacia GenerationIII spotter). Lambda DNA (20 ul; 40 ug/ml was incubated with 3 ul YOYO (neat) (Molecular Probes, Oregon).

Algorithm:
1 measure XY coordinate
2 Measure z coordinate
3 Measure physical signal (ionic current, tunneling current, FRET, quenching etc.)
4 Correlate z coordinate with physical signal
5 Move z coordinate and repeat 2-4
6 Move xy coordinate and repeat 2-5
7 Compare correlates z coordinate snd physical signal data with in silico generated location and signal data in database Example 2: Polymer Analysis It should be noted that information provided in one application below may be relevant to other applications below.

Mapping DNA Sequence

DNA is extracted so substantially long molecules can be retained, e.g., 1 kb and longer, preferably several 100 Kb in length. The DNA is arrayed on a surface so that one end can bind to the surface and the other end is free in solution. This can be achieved with a number of surface chemistries, particularly when the immobilized DNA is fragments of genomic DNA, which typically have exposed single stranded bases at the end or a free 3' or 5' OH or phosphate. In some instances the DNA is immobilised onto Poly-lysine, APTES, cyano vinyl silane coated glass surface (e.g., cover glass). In some instances the DNA is immobilised onto streptavidin coated cover glass. A variety of modified surfaces available from Microsurfaces Inc. are used from one experimental implementation to the next. High salt concentration, such as those used in the electrolytes, enable one end to remain attached while another end is free in solution.

Labels or tags are bound onto the DNA polymer either by binding alone (e.g., sequence specific inactive restriction enzymes) or by providing a mark on the DNA by a chemical or enzymatic reaction. In some embodiments the marks are created by using a nicking endonuclease to create a sequence specific nick. In some embodiments, labels are associated with the nick by extension of the 3' of the nick by labeled nucleotides using a polymerase.

The sample molecules are bathed in an electrolyte solution to which an electrode is in contact. The free end is approached by the nanopipette (by movement of the Z stage) and brought to a distance up to approximately one or a few microns from the surface (for DNA molecules of about 50 kbp in length) and the entry of the DNA into the nanopipette is detected by an ionic current blockade. After this initial ionic current blockade the substrate is translated into the Z-direction with respect to the nanopipette and changes in ionic flux are measured which relate to the position of features that are mapped onto the DNA polymer. When a feature is traversed, an increased ionic blockage is measured. In some implementation only one label or tag type is bound to the DNA polymer and is mapped. In some implementations multiple label or tag types are bound to the DNA polymer but each is distinguishable by their blocking of the ionic current to different degrees.

Sequencing Polynucleotides

DNA that is substantially double stranded is immobilised as above. A nanopipette with an embedded nanopore, as described in this disclosure but with a wide enough bore to enable double stranded DNA to translocate (e.g. ClyA) is used to interrogate the DNA molecules individually. A pattern of ionic flow characteristic to each base pair is obtained as the double stranded DNA passes the nanopore constriction. A consensus pattern is obtained by passing over the same part of the DNA multiple times (e.g., >3 times). Due to the availability of reference genome sequences and previous training with model sequences, the sequence of the interrogated DNA can be constructed. Alternatively, single stranded DNA or RNA is immobilized. When the goal is to analyse mRNA, the RNA is captured via the polyA tail by surface immobilised oligo d(t). Both RNA and DNA can be immobilized on the same surface (for example after extraction from a single cell). When the double stranded DNA has not been converted to single stranded DNA, then the RNA and DNA molecules can be distinguished by the characteristic patterns of ionic blockade due to double stranded DNA and single stranded RNA (which may or may not contain intramolecular base pairing depending on the chemical environment). When the DNA has been made fully or partially single stranded (e.g. by heat denaturation, digestion with an exonuclease) and is analyzed in denaturing environments, then both it and RNA can be interrogate at the same time, or if previously separated, then either RNA or DNA can be interrogated. The single stranded polynucleotides are interrogated with nanopores embedded in the pipettes. Each base provides a characteristic signal (e.g., change in ionic current, electron tunneling current). RNA and DNA single strands can be distinguished by the former containing uracil and the latter thymine, each with their characteristic physical signal patterns (e.g. ionic current, electron tunneling). A consensus pattern is obtained by passing over the same part of the polynucleotide multiple times (e.g., >3 times). Due to the availability of reference genome sequences and previous training with model sequences, the sequence of the interrogated polynucleotides can be constructed.

Fingerprinting Polypeptides

As a means of determining the protein composition of a sample, the protein sample (e.g., extracted from a tissue or one or more cells) is arrayed on a surface. The proteins are attached via one end. The proteins are denatured into polypeptides, e.g., by use for Guanidinium chloride and or/urea (>1M concentration). Site-Specific Protein Bioconjugation can be done via a Pyridoxal 5'-Phosphate-Mediated N-Terminal Transamination Reaction. A DNA molecule can be conjugated to the ends of all polypeptides.

Alternatively his-tagged proteins are bound to Ni-NTA or Cu-NTA coated surfaces (Microsurfaces Inc.). The molecules are arrayed far enough apart that when a nanopipette approaches the surface there is a high likelihood that only one polypeptide enters into the nanopipette.

Cysteines and lysines are labeled via the commonly used Maleimide and NHS chemistries respectively to provide a polypeptide length punctuated by site specific labels. Biotin can be added at the cysteine or lysine residues, to which a choice of avidin, streptavidin, neutravidin or anti-biotin antibody can be bound to provide a bulky label which blocks ion flow. Fluorescent labels can also be added, which in addition to blocking ionic flow can also provide a fluorescent signal, detectable by the optical detection methods of the disclosure. In addition to the voltage potential difference (which is needed for the ionic current) a negative pressure is applied to the nanopipette so that it acts to suck the free end of polypeptides on a surface. Alternatively if SDS has been applied to the polypeptide, it can move electrophoretically due to a predominant −ve charge. Translocation of the labeled polypeptide past the constriction, leads to fluxes in ionic current, whose occurrences can be correlated with the pattern of labels on the polypeptide as well as the distance of the nanopipette from the surface. The pattern of labels on an individual polypeptide is then compared to a database of polypeptide sequences (the order of amino acids) in order to identify the polypeptide, by finding an in silico match (the experimentally derived location or order of amino acids in a polypeptide corresponds to the location or order of amino acids in a polypeptide in the database).

Sequencing Polypeptide

As above, a polypeptide is attached to a surface. A nanopipette with an embedded nanopore as described in this disclosure is used to interrogate polypeptides individually. A pattern of ionic flow characteristic to each amino acid is obtained as the polypeptide passes the nanopores constriction. An average pattern can be obtained by passing over the same part of the polypeptide multiple times (e.g., >3 times). Due to the availability of reference genome sequences, RNA sequencing data and protein sequencing data, the sequence of polypeptides or polypeptide modules can be predicted. These predictions are used to "resequence" the polypeptides that are interrogated, by finding matches to predicted amino acid signal patterns of polypeptides in the database. These predicted patterns are obtained by previous creation of a training set. The training set comprises a repertoire of peptides for which ionic signals have previously been measured.

Analysing RNA from Single Cells

A culture of adherent cells (e.g., Hela cells) is mounted on the xyz stage and bathed in PBS (which acts as a low salt electrolyte solution) or in any higher salt concentration of electrolyte solution at which salt concentration the cells remain adhered to the surface. The cells are stained by calcein blue which stains the cytoplasm. This allows the cytoplasm of individual cells to be visualized. The XY stage motions are used to centre the cytoplasm at the location of the nanopipette and the Z stage is raised so that the nanopipette pierces the cell membrane and enters the cytoplasm. A positive bias is applied to the electrode within the nanopipette (and a negative bias to the electrode in the solution bathing the cells). Preferably the nanopipette contains an embedded ion channel such as MsPA. RNA molecules enter into the nanopipette and measurements are made on the lengths and physical features of the RNA, such as secondary structure, protein binding and RNA structure. The first RNA is ejected and subsequent RNA are analysed. The process is carried out in rapid succession. The measurements obtained are then used to compare to a database so that the RNA under analysis can be identified. The database may contain information about length, sequence and putative secondary structures of the RNA. Once sufficient number of RNAs have been detected, the nanopipette is withdrawn and after xy movements of the stage, a different cell is analysed. In an alternative implementation, an array of individually controllable nanopipettes take measurements of a number of cells in parallel. In another implementation, a sample of RNA from the cytoplasm from a single cell are sampled by uptake into the nanopipette (not containing an embedded ion channel) and are then ejected to form an array at a specific location on the surface (e.g., glass or plastic) at an area on which cells are not growing. This can be on the same substrate or on a different substrate. This is done such that the RNA is captured at one end. In one implementation this is done by hybridizing the poly A sequence of mRNA to oligo dT arrayed on the surface. Once the molecules are attached to the surface, the same or a different nanopores interrogates the molecules one at a time. A different nanopipette is used when an ion channel needs to be embedded in the nanopipette. For example, an embedded MsPA pore is used for sequencing of the RNA.

In an alternative embodiment cells are spread over a microwell array at dilutions that lead to individuals settling into each of the wells (although in some cases there will be more than one cell per well and other cases zero cells per well). The cells can then be lysed using for example, CelLytic-M or other detergents or by addition of Proteinase K at an appropriate temperature. The polymers of interest can become anchored to the surface, for example RNA and DNA can be come tethered to an APTES or polylysine surface. The nanopipettes can then be translated to the location of each well and move down to suck up individual biopolymers. This can be reparted within each well and after translation across an array of microwells. An array of nanopipettes can be configured to located precisely at the location of individual wells in the microwell array. Alternatively, the biopolymers can remain free in solution and the nanopipettes can suck up and eject individual biopolymers and make measurements as they do so.

Determining the Methylation Pattern Along Large Genomic Fragments

Genomic DNA is fragmented, e.g., using infrequent NOT1, PMME1 restriction enzyme and a sticky end is exposed. The short, common overhang sequence is recessed further by use of an exonuclease enzyme (e.g., T5 exonuclease). The further recessing exposes a unique sequence, that can act as a reference to a particular location in the genome. For a given genome, with a given restriction enzyme (or combination of restriction enzymes), the sequences that are expected to be exposed are determined using the tools of bioinformatics.

Oligonucleotides are made complementary to the exposed sequences and are spotted on a glass surface to make a spatially addressable microarray or a custom microarray (e.g. from Custom Array or Agilent) is obtained. A rubber gasket is attached or a barrier is created around the microarray using rubber cement/cow gum. The microarray is hydrated by pipetting buffer (e.g., TE, HEPES, PBS, 4×SSC). The sticky ends are captured by hybridization to the microarray within the confines of the barrier in 4×SSC or 3.5M TMAC1 temperatures ranging between 4 degrees C. and 55 degrees, depending on the length of exposed single strands on the target molecules. Methyl binding domain 1 protein (MBD1) is added to the array in excess in PBS. After incubation for 30 minutes to up to 24 hrs. One or more washes are conducted by adding an excess of PBS. The microarray is mounted on an XYZ stage. The captured molecules are bathed in an electrolyte solution within the confines of the barrier. A positive bias is applied to the electrode inside the nanopipette and negative bias is applied to an electrode outside the nanopipette within the solution in which the microarray is submerged. The Z axis is moved towards the nanopipette, whilst the ionic current flowing through the nanopipette is continuously monitored and feedback control is used to get to a z position which hovers above the surface (for example at a distance of 1 um from the surface) until a DNA molecule enters into the nanopipette, as detected by a drop in ionic current. The DNA molecule becomes extended within the nanopipetted and the nanopipette is withdrawn from the surface, whilst traversing the terrain of the DNA strand. A further drop in ionic current represents a putative site of MBD1 binding. As the MBD1 traverses past the constriction, the ionic current rises again. The ionic current dips again when the next MBD1 is encountered the location of the MBD1 is measured. The spikes and dips in ionic current are recorded as a function of distance from the surface. The molecule is measure 3-10× by up and down motions of the Z axis. The molecule is ejected b lowering the Z stage or by reversing the voltage. The stage is translated in the X or Y direction to move another microarray spot within the range of the nanopipette. In an alternative embodiment, the spacing of the spots corresponds to the spacing of the nanopipettes and each spot is measured simultaneously. As it is known which genomic fragments are captured by hybridization to which spots, the capture point provides a reference sequence in relation to which the methylation locations are recorded. The methylation locations can also be related to other mapped sites on the molecule, for example by the mapping of the binding of inactivated restriction enzymes, PNA probes, cas9 mediated guideRNA binding etc.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should be appreciated that features of separately-recited embodiments can be combined in any desired combination which may be apparent to those skilled in the art.

What is claimed is:

1. A method for analyzing one or more macromolecules, the method comprising:
   i. attaching one or more macromolecules to a fixed location on a solid phase surface;
   ii. providing a first electrode in fluidic communication with said one or more macromolecules through an ionic aqueous buffer;
   iii. providing a nanopipette containing a second electrode;
   iv. applying a potential difference between the first and second electrodes to induce the flow of ions;
   v. bringing the nanopipette in sufficient proximity to a macromolecule such that the macromolecule enters into the nanopipette; and
   vi. measuring an ion flow.

2. The method of claim 1, optionally measuring ion flow prior to and after the macromolecule enters the nanopipette.

3. A method according to claim 1, wherein the macromolecule is a polymer.

4. A method according to claim 3, wherein the polymer is a nucleic acid or peptide.

5. A method according to claim 4, wherein the first electrode has a −ve bias and the second electrode has +ve bias.

6. A method according to claim 5, wherein the nucleic acid is electrophoretically stretched towards the second electrode (+ve bias) due to its negatively charged backbone.

7. A method according to claim 6, wherein the nanopipette is translated in the Z direction with respect to the surface.

8. A method according to claim 6, wherein a change in ion flux is measured as the nanopipette is translated in the z direction with respect to the surface.

9. A method according to claim 8, wherein level of ion flux is correlated with z position.

10. A method according to claim 9, wherein the nanopipette to surface distance is varied repetitively.

11. A method according to claim 10, wherein the repeated measurements are used to obtain an average measurement.

12. A method according to claim 11, wherein the molecule is a nucleic acid and the average measurement is used to make a base call.

13. A method according to claim 11, wherein the macromolecule is a polypeptide and the average measurement is used to detect an amino acid of the polypeptide.

14. A method according to claim 10, wherein the macromolecule is a nucleic acid and a base call is made for each repetition.

15. A method according to claim 10, wherein the macromolecule is a polypeptide and the average measurement is used to detect an amino acid of the polypeptide for each repetition.

16. A method according to claim 1 wherein the macromolecule is released from the nanopipette.

17. A method according to claim 16, wherein the macromolecule is captured again by the nanopipette.

18. A method according to claim 16, wherein the solid phase surface is mounted on a stage which is translated in the X or Y direction in relation to the nanopipette or vice versa.

19. A method according to claim 18, wherein a second macromolecule enters into the nanopipette.

20. A method according to claim 19, wherein one or more of steps i and vi are repeated for the second macromolecule.

21. A method according to claim 1, wherein the macromolecule enters the nanopipette through a biological nanopore embedded on an aperture of the nanopipette in sufficient proximity to the macromolecule.

22. A method for analyzing one or more macromolecules selected from the group consisting of nucleic acids and polypeptides, the method comprising:
  i. attaching one or more macromolecules to a fixed location on a solid phase surface;
  ii. providing a first electrode in fluidic communication with said one or more macromolecules through an ionic aqueous buffer;
  iii. providing a nanopipette containing a second electrode;
  iv. applying a potential difference between the first and second electrodes to induce the flow of ions;
  v. bringing the nanopipette in sufficient proximity to a macromolecule such that the macromolecule enters into the nanopipette; and
  vi. measuring an ion flow.

* * * * *

SEQUENCE LISTING

```
<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 1
gggcggcgac ct                                                       12

<210> SEQ ID NO 2
<211> LENGTH: 12
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 2
aggtcgccgc cc                                                       12
```